US011883482B2

(12) United States Patent
Zheng et al.

(10) Patent No.: US 11,883,482 B2
(45) Date of Patent: Jan. 30, 2024

(54) RECOMBINANT NUCLEIC ACID OF SENECA VALLEY VIRUS, RECOMBINANT VACCINE STRAIN AND PREPARATION METHOD AND USE THEREOF

(71) Applicant: Lanzhou Veterinary Research Institute, Chinese Academy of Agricultural Sciences, Lanzhou (CN)

(72) Inventors: Haixue Zheng, Lanzhou (CN); Fan Yang, Lanzhou (CN); Zixiang Zhu, Lanzhou (CN); Weijun Cao, Lanzhou (CN); Hong Tian, Lanzhou (CN); Keshan Zhang, Lanzhou (CN); Ting Wei, Lanzhou (CN); Min Zheng, Lanzhou (CN); Wei Zhang, Lanzhou (CN); Wen Dang, Lanzhou (CN); Xusheng Ma, Lanzhou (CN); Dan Li, Lanzhou (CN); Yi Ru, Lanzhou (CN); Jijun He, Lanzhou (CN); Jianhong Guo, Lanzhou (CN); Xiangtao Liu, Lanzhou (CN)

(73) Assignee: Lanzhou Veterinary Research Institute, Chinese Academy of Agricultural Sciences

( * ) Notice: Subject to any disclaimer, the term of this patent is extended or adjusted under 35 U.S.C. 154(b) by 267 days.

(21) Appl. No.: 17/328,135

(22) Filed: May 24, 2021

(65) Prior Publication Data
US 2022/0031832 A1    Feb. 3, 2022

(30) Foreign Application Priority Data
Mar. 24, 2020 (CN) .......................... 202010212460.6

(51) Int. Cl.
| | | |
|---|---|---|
| C12N 7/00 | (2006.01) | |
| C12N 15/66 | (2006.01) | |
| C12N 15/10 | (2006.01) | |
| A61K 39/125 | (2006.01) | |
| A61K 39/00 | (2006.01) | |

(52) U.S. Cl.
CPC .......... *A61K 39/125* (2013.01); *C12N 15/102* (2013.01); *C12N 15/66* (2013.01); *A61K 2039/5252* (2013.01); *A61K 2039/53* (2013.01); *C12N 7/00* (2013.01); *C12N 2770/32034* (2013.01)

(58) Field of Classification Search
None
See application file for complete search history.

*Primary Examiner* — Nicole Kinsey White
(74) *Attorney, Agent, or Firm* — Brian M. Kaufman; Robert D. Atkins; PATENT LAW GROUP: Atkins and Associates, P.C.

(57) ABSTRACT

The disclosure provides a recombinant nucleic acid of Seneca valley virus, a recombinant vaccine strain and preparation method and use thereof, and relates to the technical field of genetic engineering. The disclosure provides the recombinant nucleic acid of Seneca valley virus, recombinant Seneca valley virus comprising the recombinant nucleic acid, recombinant Seneca valley virus encoded by the recombinant nucleic acid, recombinant Seneca valley virus vaccine strain comprising the recombinant Seneca valley virus and preparation method and use thereof. According to the disclosure, a vaccine strain characterized by high antigen production capacity, remarkably reduced pathogenicity (even having no pathogenicity to pigs), strong antibody induction activity, high immune protection rate is prepared. The vaccine strain remarkably improves the biological safety and can be used for preventing and controlling Seneca valley virus in China and the neighboring countries.

15 Claims, 3 Drawing Sheets
Specification includes a Sequence Listing.

RECOMBINANT NUCLEIC ACID OF SENECA VALLEY VIRUS, RECOMBINANT VACCINE STRAIN AND PREPARATION METHOD AND USE THEREOF

CROSS REFERENCE TO RELATED APPLICATION

The present application claims the benefit and priority of Chinese Patent Application No. 202010212460.6 filed on Mar. 24, 2020, the disclosure of which is incorporated by reference herein in its entirety as part of the present application.

TECHNICAL FIELD

The disclosure belongs to the technical field of genetic engineering, and particularly relates to a recombinant nucleic acid of Seneca valley virus, a recombinant vaccine strain and preparation method and use thereof.

BACKGROUND ART

Senecavirus A (SVA), also known as Seneca valley virus (SVV), belongs to the *Senecavirus* genus of Picornaviridae and is the only member of this genus. The virus can cause primary vesicular disease in pigs, which is difficult to distinguish from clinical symptoms caused by foot-and-mouth disease, swine vesicular disease and vesicular stomatitis. SVV infection can cause vesicular lesions in pigs of all ages of weaning, nursing, fattening and breeding, accompanied by clinical symptoms such as claudication, fever, anorexia and lethargy. Besides the above symptoms, the newborn piglets may also have symptoms of persistent diarrhea, dehydration and the like, even sudden death.

Seneca valley virus was first isolated from pollutants in cell culture medium by American researchers in 2002. At first, Seneca valley virus is not associated with any disease, but used for the treatment of human cancer by using its oncolytic properties, it is found until 2007 that Seneca valley virus can infect pigs and cause porcine idiopathic vesicular disease (PIVD). Since 2014-2015, Seneca valley virus has been widely spread in many countries, and its transmission speed and pathogenicity have enhanced compared with the cases reported previously, the situation of prevention and control is still grim.

SUMMARY

In view of this, the object of the present disclosure is to provide a recombinant nucleic acid of Seneca valley virus, a recombinant Seneca valley virus comprising the recombinant nucleic acid, a recombinant Seneca valley virus encoded by the recombinant nucleic acid, a recombinant Seneca valley virus vaccine strain comprising the recombinant Seneca valley virus and preparation method and use thereof. According to the disclosure, a vaccine strain characterized by high antigen production capacity, remarkably reduced pathogenicity (even having no pathogenicity to pigs), strong antibody induction activity, high immune protection rate is prepared. The vaccine strain remarkably improves the biological safety and can be used for preventing and controlling Seneca valley virus in China and the neighboring countries.

In order to achieve the above object of the disclosure, the present disclosure provides the following technical solution:

The present disclosure provides a recombinant nucleic acid of Seneca valley virus, wherein the sequence of the recombinant nucleic acid comprises deletion and mutation on 5'UTR gene sequence of the Seneca valley virus strain.

In some embodiments, the nucleotide sequence of the 5'UTR gene modified by deletion and mutation of the 5'UTR gene sequence of Seneca valley virus strain is set forth in SEQ ID NO:1.

In some embodiments, the Seneca valley virus strain comprises SVV/FJ/001 strain.

The present disclosure also provides the use of the recombinant nucleic acid in preparing recombinant nucleic acid of Seneca valley virus or recombinant Seneca valley virus vaccine strain.

The present disclosure also provides a recombinant Seneca valley virus comprising the recombinant nucleic acid.

The present disclosure also provides a recombinant Seneca valley virus encoded by the recombinant nucleic acid.

The present disclosure also provides a recombinant Seneca valley virus vaccine strain comprising the recombinant Seneca valley virus.

In some embodiments, the recombinant Seneca valley virus vaccine strain can induce the immune response in animals against Seneca valley virus.

In some embodiments, the values of the 50% protection dose ($PD_{50}$) of the recombinant Seneca valley virus vaccine strains against the Seneca valley virus isolates are all greater than 6.

The present disclosure also provides the constructing method of recombinant Seneca valley virus, wherein comprising:

(1) using a cDNA of SVV/FJ/001 strain as template, a S1 fragment and a S2 fragment of SVV/FJ/001 strain were amplified with specific primer pairs respectively; the specific primer pair for amplifying the S1 fragment comprises two forward primers and a reverse primer SVA-1R, wherein the forward primers comprise SVA-1F0 and SVA-1F; the nucleotide sequence of the forward primer SVA-1F0 is set forth in SEQ ID NO:2, the nucleotide sequence of the forward primer SVA-1F is set forth in SEQ ID NO:3, and the nucleotide sequence of the reverse primer SVA-1R is set forth in SEQ ID NO:4;

a specific primer pair for amplifying the S2 fragment comprises a forward primer SVA-2F and a reverse primer SVA-2R, wherein the nucleotide sequence of the forward primer SVA-2F is set forth in SEQ ID NO:5, and the nucleotide sequence of the reverse primer SVA-2R is set forth in SEQ ID NO:6;

(2) ligating the S1 fragment and S2 fragment with pMD20 T vector respectively to obtain subclone plasmids PMD-S1 and PMD-S2;

(3) using the subclone plasmid PMD-S1 as a template, amplifying the PMD-S1 with mutation primers SVA-m5UTRF and SVA-m5UTRR to obtain subclone plasmid PMD-mS1, wherein the nucleotide sequence of SVA-m5UTRF is set forth in SEQ ID NO:7, and the nucleotide sequence of SVA-m5UTRR is set forth in SEQ ID NO: 8;

(4) after digesting the plasmid PMD-mS1 with PacI and SphI, and digesting the plasmid PMD-S2 with SphI and NotI, collecting the gene fragments and inserting into eukaryotic transcription plasmid prO/CHA/99 digested with PacI and NotI, thus obtaining the recombinant plasmid prSVV/FJ-M;

(5) transfecting the Seneca valley virus sensitive cells with the obtained eukaryotic transcription plasmid prSVV/FJ-M to obtain the recombinant Seneca valley virus.

In some embodiments, the mutated 5'UTR gene fragment in step (3) comprises the nucleic acid sequence set forth in SEQ ID NO:1, or comprises the recombinant nucleic acid.

In some embodiments, the Seneca valley virus sensitive cells in step (5) comprises BHK-21 cells, PK-15 cells, ST cells, SK-RST cells, IBRS-2 cells, H1299 cells or 293 T cells.

In some embodiments, the recombinant Seneca valley virus obtained in step (5) is suitable for suspension cell culture.

The present disclosure also provides the use of the recombinant Seneca valley virus or the recombinant Seneca valley virus prepared by the constructing method in preparing recombinant Seneca valley virus vaccine.

The present disclosure also provides a preparation method of recombinant Seneca valley virus vaccine, wherein comprising:
1) inoculating recombinant Seneca valley virus into susceptible cells for proliferation culture to obtain a recombinant Seneca valley virus solution;
2) inactivating and emulsifying the recombinant Seneca valley virus in the recombinant Seneca valley virus solution to obtain the recombinant Seneca valley virus vaccine.

In some embodiments, the susceptible cells in step 1) comprise BHK-21 cells, PK-15 cells, ST cells, SK-RST cells, IBRS-2 cells, H1299 cells or 293 T cells.

In some embodiments, the susceptible cells in step 1) comprise suspension cells of BHK-21 cells, PK-15 cells, ST cells, SK-RST cells, IBRS-2 cells, H1299 cells or 293 T cells.

In some embodiments, during the proliferation culture in step 1), the virus titer of the recombinant Seneca valley virus is not lower than $10^{6.5}$ $TCID_{50}$/mL.

In some embodiments, the inactivation in step 2) is carried out by using binary ethylenimine.

In some embodiments, the concentration of the binary ethylenimine in the inactivated system is 1.5 mmol/L.

In some embodiments, the inactivation temperature is 30° C., and the inactivation time is 36 hours.

In some embodiments, during the emulsification in step 2), the inactivated recombinant Seneca valley virus and ISA 206 adjuvant are mixed in a volume ratio of 1:1.

The present disclosure also provides a recombinant Seneca valley virus vaccine prepared by the above preparation method.

The present disclosure also provides the use of the recombinant Seneca valley virus vaccine strain or the recombinant Seneca valley virus vaccine in preparing drugs for preventing and/or controlling related diseases caused by Seneca valley virus in animals.

In some embodiments, the animals comprise pig, cattle or sheep.

The disclosure provides a recombinant nucleic acid of Seneca valley virus, a recombinant virus, a recombinant Seneca valley virus vaccine strain comprising the recombinant Seneca valley virus and preparation method and use thereof. According to the Seneca valley virus molecular epidemiology and the resources of epidemic strains accumulated in the early stage, the full-length cDNA modified by gene deletion and mutation of SVV/FJ/001 strain is constructed by using the established high-efficiency reverse genetic operation technology platform. After virus rescue, biological characteristics determination of recombinant strain, suspension cell culture adaptation, pathogenicity research, vaccine efficacy evaluation, etc., the results show that the obtained recombinant Seneca valley virus not only has the characteristics of high virus titer and adaptability to suspension cell culture, but also has significantly reduced pathogenicity to pigs, even has no pathogenicity to pigs, thus significantly improving biosafety. The vaccine prepared with this recombinant Seneca valley virus strain has the characteristics of good antibody response and high immune protection efficiency, which has significantly improved biosafety, and can be used for the prevention and control of Seneca valley virus in China and the neighboring countries.

The antigen gene P1 of SVV/FJ/001 strain of the present disclosure has more than 98.6% homology with the isolated Seneca valley virus epidemic strain reported in China, and also has high homology with the epidemic strains in other countries. P1 gene is the antigen gene of Seneca valley virus, and the generated antigen can induce production of neutralizing antibodies in animals. Therefore, by using SVV/FJ/001 strain as template, using reverse genetic operation technology, the recombinant Seneca valley virus strain is constructed through amplification and modification, wherein the obtained recombinant Seneca valley virus strain has high antigen matching and immune response of vaccine strain, ensures pertinence of vaccine strain to epidemic strain, and can be used as a good vaccine candidate strain for prevention and control of Seneca valley virus in China and other countries.

The recombinant Seneca valley virus rSVV/FJ-M of the present disclosure has high virus titer, the cytopathic effect time after stable passage is about 12-18 hours, and the virus titer is $10^{6.5}$ $TCID_{50}$/ml-$10^{10.0}$ $TCID_{50}$/ml. The rSVV/FJ-M strain can adapt to suspension cell culture and improve virus productivity, which lays a foundation for large-scale and industrial production of Seneca vaccine.

In the Examples of the present disclosure, the recombinant Seneca valley virus rSVV/FJ-M is also prepared into inactivated vaccine, and the immune efficacy and cross-challenge tests are carried out. The results show that the inactivated vaccine prepared by the recombinant strain can effectively provide protection in animals against a variety of Seneca valley virus isolated strains, such as epidemic strains isolated in Fujian, Henan and Guangdong, China, with $PD_{50}$ of 15.59, 13.59 and 13.59 respectively, thus broad spectrum of antigens of the recombinant vaccine strain can be achieved.

The 5'UTR of the recombinant Seneca valley virus rSVV/FJ-M is modified by partial deletion and mutation. Compared with the pathogenicity of SVV/FJ/001, the virulence of the strain to pigs is significantly reduced, even having no pathogenicity to pigs, and the biosafety is significantly improved.

The technology of the disclosure achieves a more active and effective constructing mode of the Seneca valley virus vaccine strain, and further realizes the innovation of the preparation techniques of virus seeds for the Seneca valley virus vaccines, and has significant application value.

DETAILED DESCRIPTION OF THE EMBODIMENTS

Figure 1:
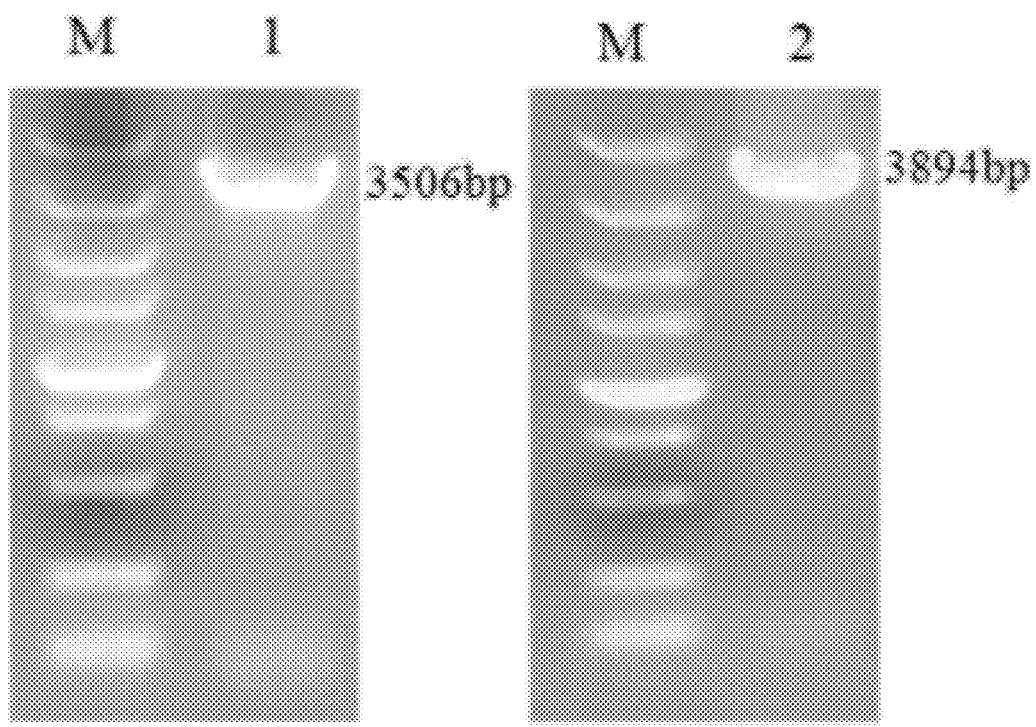
FIG. 1 is the electrophoresis results of amplified Seneca valley virus S1 and S2 fragments in Example 1, where band "1" is the amplified product of S1 fragment; band "2" is the amplified product of S2 fragment; M is DL5000 DNA marker.

The present disclosure provides a recombinant nucleic acid of Seneca valley virus, wherein the sequence of the recombinant nucleic acid comprises deletion and mutation modification on 5'UTR gene sequence of Seneca valley virus strain.

The Seneca valley virus strain of the present disclosure preferably comprises SVV/FJ/001 strain. The SVV/FJ/001 strain of the present disclosure is preferably the Seneca Valley virus FJ/001 (SVV/FJ/001) that is preserved in China Center for Type Culture Collection (CCTCC) with the preservation number of CCTCC NO.V201802, and has been disclosed in the Chinese issued patent "Seneca valley virus vaccine and preparation method and use thereof" (ZL201810003888.2). The depository address for CCTCC is College of Life Sciences, Wuhan University, Wuhan, China 430072. Deposit was made on Dec. 7, 2017.

The 5'UTR gene sequence of SVV/FJ/001 strain in the present disclosure is preferably modified by deletion and mutation, and the nucleotide sequence of the 5'UTR gene of SVV/FJ/001 strain modified is set forth in SEQ ID NO:1.

The present disclosure also provides the use of the recombinant nucleic acid in preparing recombinant nucleic acid of Seneca valley virus or recombinant Seneca valley virus vaccine strain.

The present disclosure also provides a recombinant Seneca valley virus comprising the recombinant nucleic acid.

The present disclosure also provides a recombinant Seneca valley virus encoded by the recombinant nucleic acid.

In the present disclosure, the recombinant Seneca valley virus strain is preferably named rSVV/FJ-M strain.

The present disclosure also provides a recombinant Seneca valley virus vaccine strain comprising the recombinant Seneca valley virus.

The recombinant Seneca valley virus vaccine strain of the present disclosure can stimulate the immune activity of animals against Seneca valley virus; the values of the 50% protection dose ($PD_{50}$) of the recombinant Seneca valley virus vaccine strains against the Seneca valley virus isolates are all greater than 6.

The present disclosure also provides the constructing method of recombinant Seneca valley virus, wherein comprising:
(1) using a cDNA of SVV/FJ/001 strain as template, a S1 fragment and a S2 fragment of SVV/FJ/001 strain were amplified with specific primer pairs respectively; the specific primer pair for amplifying the S1 fragment comprises two forward primers and a reverse primer SVA-1R, wherein the forward primers comprise SVA-1F0 and SVA-1F; the nucleotide sequence of the forward primer SVA-1F0 is set forth in SEQ ID NO:2, the nucleotide sequence of the forward primer SVA-1F is set forth in SEQ ID NO:3, and the nucleotide sequence of the reverse primer SVA-1R is set forth in SEQ ID NO:4;
a specific primer pair for amplifying the S2 fragment comprises a forward primer SVA-2F and a reverse primer SVA-2R, wherein the nucleotide sequence of the forward primer SVA-2F is set forth in SEQ ID NO:5, and the nucleotide sequence of the reverse primer SVA-2R is set forth in SEQ ID NO:6;
(2) ligating the S1 fragment and S2 fragment with pMD20 T vector respectively to obtain subclone plasmids PMD-S1 and PMD-S2;
(3) using the subclone plasmid PMD-S1 as a template, amplifying the PMD-S1 with mutation primers SVA-m5UTRF and SVA-m5UTRR to obtain subclone plasmid PMD-mS1, wherein the nucleotide sequence of SVA-m5UTRF is set forth in SEQ ID NO:7, and the nucleotide sequence of SVA-m5UTRR is set forth in SEQ ID NO: 8;
(4) after digesting the plasmid PMD-mS1 with PacI and SphI, and digesting the plasmid PMD-S2 with SphI and NotI, collecting the gene fragments and inserting into eukaryotic transcription plasmid prO/CHA/99 digested with PacI and NotI, thus obtaining the recombinant plasmid prSVV/FJ-M;
(5) transfecting the Seneca valley virus sensitive cells with the obtained eukaryotic transcription plasmid prSVV/FJ-M to obtain the recombinant Seneca valley virus.

According to the disclosure, the cDNA of SVV/FJ/001 strain is used as a template, and the S1 fragment and S2 fragment of SVV/FJ/001 strain are amplified by using specific primer pairs, respectively; the specific primer pair for amplifying the S1 fragment comprises two forward primers and a reverse primer SVA-1R, wherein the forward primers comprise SVA-1F0 and SVA-1F; the nucleotide sequence of the forward primer SVA-1F0 is set forth in SEQ ID NO:2, the nucleotide sequence of the forward primer SVA-1F is set forth in SEQ ID NO:3, and the nucleotide sequence of the reverse primer SVA-1R is set forth in SEQ ID NO:4; the specific primer pair for amplifying the S2 fragment comprises a forward primer SVA-2F and a reverse primer SVA-2R, wherein the nucleotide sequence of the forward primer SVA-2F is set forth in SEQ ID NO:5, and the nucleotide sequence of the reverse primer SVA-2R is set forth in SEQ ID NO:6. The present disclosure has no special limitation on the resource of the cDNA of the SVV/FJ/001 strain, which is preferably obtained by extracting RNA and then performing reverse transcription experiment.

The name and sequence of the specific primer pair for amplification in the present disclosure are shown as follows:

(SEQ ID NO: 2)
SVA-1F0: 5'-gtgaggacgaaactataggaaaggaattcctatagt cttgaaagggggggctgggcc-3';

(SEQ ID NO: 3)
SVA-1F: 5'-ataggtttaattaatgttaagcgtctgatgagtccgt gaggacgaaactatagga-3', and the underlined part is PacI restriction enzyme cutting site;

SVA-1R: 5'-gggaagcatgctggggcaccaggcac-3'(SEQ ID NO:4), and the underlined part is SphI restriction enzyme cutting site;

SVA-2F: 5'-ccccagcatgcttcccttcgcagc-3' (SEQ ID NO:5), and the underlined part is SphI restriction enzyme cutting site;

SVA-2R: 5'-tttttctagagcggccgct$_{38}$-3'(SEQ ID NO:6), and the underlined part is NotI restriction enzyme cutting site, the t38 represents the Poly(T) of 38 nt.

In the present disclosure, the first amplification is preferably carried out with the primers SVA-1F0 and SVA-1R, and then the amplified products are used as template to perform the second amplification with the primers SVA-1F and SVA-1R to obtain the S1 fragment.

The amplification system and program of the S1 fragment and S2 fragment preparation are not particularly limited in the present disclosure, and it is preferable to be carried out according to the method described in the "Short Protocols in Molecular Biology" (edited by F. M. Osberg, R. E. Kingston, J. G. Seidemann, etc., translated by Ma Xuejun and Shu Yuelong, Beijing: Science Press, 2004).

After obtaining S1 fragment and S2 fragment, the S1 fragment and S2 fragment in the present disclosure are ligated with pMD20 T vector respectively to obtain subclone plasmids PMD-S1 and PMD-S2. According to the disclosure, the S1 fragment and the S2 fragment are preferably collected from the obtained amplification products by agarose gel electrophoresis and gel extraction.

After obtaining subclone plasmids PMD-S1 and PMD-S2, the disclosure uses the subclone plasmid PMD-S1 as a template, and the subclone plasmid PMD-mS1 is generated using the mutation primers SVA-m5UTRF and SVA-m5UTRR, wherein the nucleotide sequence of SVA-m5UTRF is set forth in SEQ ID NO:7, and the nucleotide sequence of SVA-m5UTRR is set forth in SEQ ID NO: 8;

The sequences of the mutation primers in the present disclosure are as follows:

(SEQ ID NO: 7)
SVA-m5UTRF: 5'-gttctagcctactcgttttttcccctactcact cattcgtgttgtaactacaggat-3';

(SEQ ID NO: 8)
SVA-m5UTRR: 5'-atcctgtagttacaacacgaatgagtgagtagg ggaaaaaacgagtaggctagaac-3'.

Preferably, the mutated 5'UTR gene fragment comprises a nucleic acid sequence set forth in SEQ ID NO:1, or comprises the recombinant nucleic acid.

According to the disclosure, the plasmid PMD-mS1 is digested with PacI and SphI, and the plasmid PMD-S2 is digested with SphI and NotI, and then the gene fragments are collected and purified, and then inserted into the eukaryotic transcription plasmid prO/CHA/99 vector digested with PacI and NotI, thus obtaining the recombinant plasmid prSVV/FJ-M. The recombinant plasmid prSVV/FJ-M comprises the modified SVV/FJ/001 full-length gene.

The Seneca valley virus sensitive cells are transfected with the recombinant plasmid prSVV/FJ-M to obtain the recombinant Seneca valley virus. The Seneca valley virus sensitive cells of the present disclosure preferably comprise BHK-21 cells, PK-15 cells, ST cells, SK-RST cells, IBRS-2 cells, H1299 cells or 293 T cells. The recombinant Seneca valley virus obtained by the disclosure is preferably suitable for suspension cell culture.

The present disclosure also provides the use of the recombinant Seneca valley virus or the recombinant Seneca valley virus prepared by the constructing method in preparing recombinant Seneca valley virus vaccine.

The present disclosure also provides a preparation method of recombinant Seneca valley virus vaccine, wherein comprising:

1) inoculating recombinant Seneca valley virus into susceptible cells for proliferation culture to obtain a recombinant Seneca valley virus solution;

2) inactivating and emulsifying the recombinant Seneca valley virus in the recombinant Seneca valley virus solution to obtain the recombinant Seneca valley virus vaccine.

In the present disclosure, the susceptible cells in step 1) preferably comprise BHK-21 cells, PK-15 cells, ST cells, SK-RST cells, IBRS-2 cells, H1299 cells or 293 T cells, more preferably BHK-21 suspension cells or ST suspension cells.

In the present disclosure, during the proliferation culture in step 1), the virus titer of the recombinant Seneca valley virus is preferably not lower than $10^{6.5}$ $TCID_{50}$/mL, more preferably $10^{6.5}$ $TCID_{50}$/ML-$10^{10.0}$ $TCID_{50}$/mL. The recombinant Seneca valley virus strain in the disclosure has high titer when being proliferated in the susceptible cells, which can well adapt to cell proliferation, and has high antigen productivity.

In the present disclosure, the inactivation in step 2) is preferably carried out by using binary ethylenimine. The concentration of the binary ethylenimine in the inactivated system is preferably 1.5 mmol/L. The inactivation temperature is preferably 30° C., and the inactivation time is preferably 36 hours.

In the present disclosure, during the emulsification in step 2), the inactivated recombinant Seneca valley virus and ISA 206 adjuvant are preferably mixed in a volume ratio of 1:1.

The present disclosure also provides a recombinant Seneca valley virus vaccine prepared by the preparation method.

The recombinant Seneca valley virus vaccine of the present disclosure can induce the immune response in animals against Seneca valley virus strains, and the Seneca valley virus strains preferably include SVV/FJ/001 strain, SVV-HN strain (Henan strain) and SVV-GD strain (Guangdong strain), and the $PD_{50}$ values of recombinant Seneca valley virus vaccine strain to SVV/FJ/001 strain, SVV-HN strain and SVV-GD strain are all greater than 6.

The disclosure also provides the use of the recombinant Seneca valley virus vaccine in preparing drugs for preventing and/or controlling related diseases of animals caused by Seneca valley virus.

The animal of that present disclosure preferably include pigs, cattle or sheep. The Seneca valley virus of the present disclosure preferably includes SVV/FJ/001 strain, SVV-HN strain or SVV-GD strain.

A recombinant nucleic acid of Seneca valley virus and use thereof provided by the present disclosure will be described in detail with examples below, but they cannot be understood as limiting the scope of protection of the present disclosure.

Unless otherwise specified, the experimental methods used in the following examples are all carried out under conventional conditions, such as the methods described in "Short Protocols in Molecular Biology" (edited by F. M. Osberg, R. E. Kingston, J. G. Seidemann, etc., translated by Ma Xuejun and ShuYuelong, Beijing: Science Press, 2004).

Example 1

Construction of Infectious Clones of Recombinant Seneca Valley Virus:

The virus strain SVV/FJ/001 was preserved in China Center for Type Culture Collection (microbial preservation number: CCTCC NO.V201802) (disclosed in the issued patent "Seneca valley virus vaccine and preparation method and use thereof" ZL201810003888.2, the disclosure of which is incorporated by reference herein in its entirety as part of the present application), according to the Seneca valley virus genomic sequence (Genebank: KY747510), the amplified primers were designed and synthesized:

(SEQ ID NO: 2)
SVA-1F0: 5'-gtgaggacgaaactataggaaaggaattcctatagtc ttgaaagggggggctgggcc-3';

(SEQ ID NO: 3)
SVA-1F: 5'-ataggtttaattaatgttaagcgtctgatgagtccgtg aggacgaaactatagga-3';

(SEQ ID NO: 4)
SVA-1R: 5'-gggaagcatgctggggcaccaggcac-3';

(SEQ ID NO: 5)
SVA-2F: 5'-ccccagcatgcttcccttcgcagc-3';

(SEQ ID NO: 6)
SVA-2R: 5'-ttttctagagcggccgct$_{38}$-3'.

(SEQ ID NO: 7)
SVA-m5UTRF: 5'-gttctagcctactcgttttttcccctactcactca ttcgtgttgtaactacaggat-3';

(SEQ ID NO: 8)
SVA-m5UTRR: 5'-atcctgtagttacaacacgaatgagtgagtagggg aaaaaacgagtaggctagaac-3'.

Among the above specific primers, the forward primers SVA-1F and SVA-1F0 used to amplify S1 fragment were introduced with PacI restriction enzyme site and core sequence of hammerhead ribozyme, so as to ensure that infectious viral RNA was generated after transcription and shearing modification, and the reverse primer SVA-1R contained SphI restriction enzyme site. The forward primer SVA-2F for amplifying S2 fragment contained SphI restriction enzyme site, and the reverse primer SVA-2R contained NotI restriction enzyme site and poly(T) of 38 nt. SVA-m5UTRF and SVA-m5UTRR were primers for deletion and site-directed mutation of 5'UTR gene in S1 fragment.

Total RNA of SVV/FJ/001 was extracted by Trizol reagent or RNA extraction kit), the first strand cDNA was synthesized by reverse transcription with primer SVA-2R, and a 204, reaction system was prepared by reverse transcriptase, reacting at 42° C. for 1 h for later use. The first strand cDNA of reverse transcription was used as template, and amplified with primers SVA-1F and SVA-1R, then the amplified product was used as template to perform the second amplification with primers SVA-1F and SVA-1R to obtain a first gene fragment S1; the first strand cDNA of reverse transcription was used as template, and amplified with primers SVA-2F and SVA-2R to obtain a second gene fragment S2. During the above amplification, a 50 μL reaction system was prepared by using DNA polymerase which was suitable for long fragment amplification and has excellent performance, and the amplification conditions were as follows: 94° C. for 5 min; 94° C. for 30 s, 57° C. for 30 s, 72° C. for 3 min and 30 s, 35 cycles; 72° C. for 10 min, the PCR amplified products were purified and collected. The electrophoresis results of the amplified products were shown in FIG. 1, the sizes of S1 and S2 were 3506 bp and 3894 bp, respectively, which were consistent with the expected size.

The above S1 and S2 gene fragments were collected by gel extraction, ligated with pMD20 T vector, transformed into JM109 competent cells, screened and sequenced to identify positive clones, which were named PMD-S1 and PMD-S2 respectively. The plasmid PMD-S1 was used as template and amplified with primers SVA-m5UTRF and SVA-m5UTRR, the 5'UTR gene on S1 fragment was deleted and mutated. As for the amplification, a 50 μL reaction system was prepared by DNA polymerase with high fidelity, and the amplification conditions were: 95° C. for 5 min; 95° C. for 1 min, 55° C. for 1 min, 68° C. for 6 min, 20 cycles; 68° C. for 10 min, the amplified products were digested with DpnI to remove the template plasmid, and then transformed into DH5α competent cells, screened and sequenced to identify positive clones, which were named PMD-mS1. The sequencing results showed that mS1 contained the 5'UTR gene which is modified by deletion and mutation, which was set forth in SEQ ID NO:1.

Figure 2:
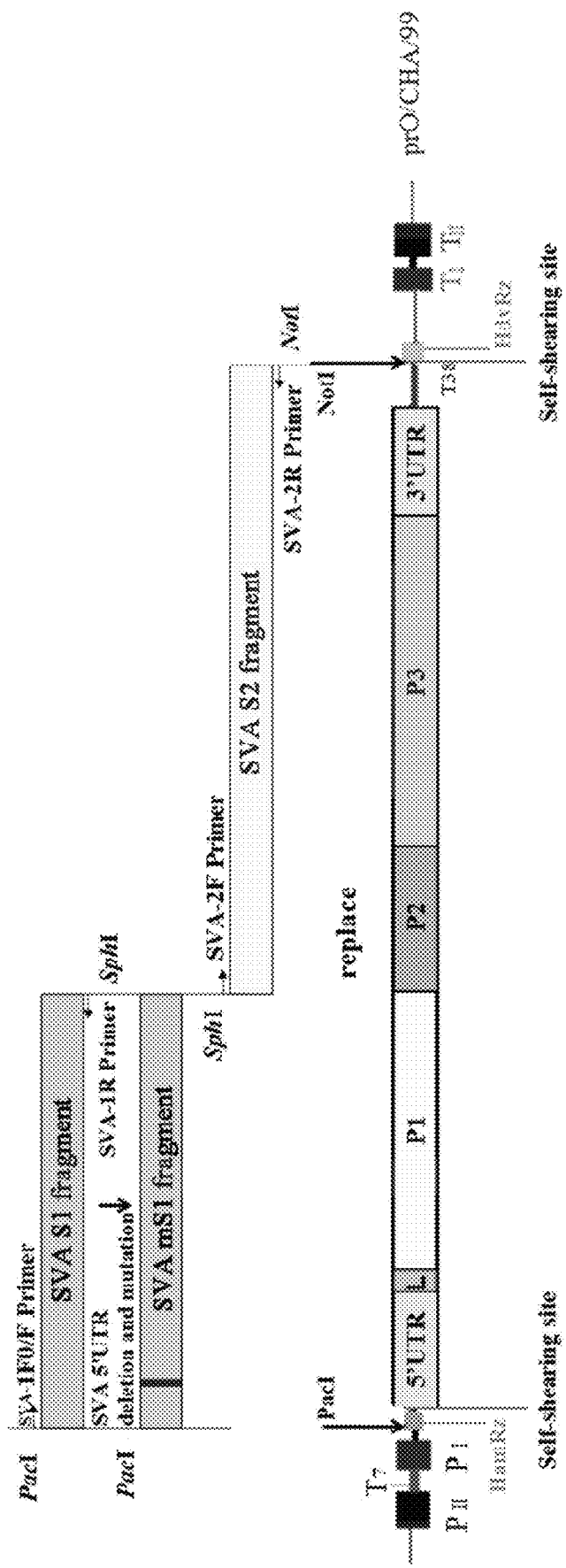
FIG. 2 is a schematic diagram of the constructing method of Seneca valley virus recombinant plasmid prSVV/FJ-M in Example 1.

The plasmid PMD-mS1 was digested with PacI and SphI, and the plasmid PMD-S2 was digested with SphI and NotI, then the target fragments were collected respectively. Then, the plasmid prO/CHA/99 comprising O/CHA/99 strain rescue system of foot-and-mouth disease virus type μL (disclosed in the issued patents ZL201310175323.X, "Recombinant virus of Asia1 foot and mouth disease and preparation method and use thereof" and ZL201310175324.4, "Recombinant vaccine strain of foot-and-mouth disease type A and preparation method and use thereof", the disclosures of which are incorporated by reference herein in their entireties as part of the present application) was digested with PacI and NotI, and the vector fragment was purified and collected, which was ligated with T4 ligase and transformed into JM109 competent cells, after digestion and sequencing to identify the positive clones, the recombinant plasmid prSVV/FJ-M comprising the modified SVV/FJ/001 full-length gene was obtained, the constructing method was shown in FIG. 2.

Example 2

Figure 3:
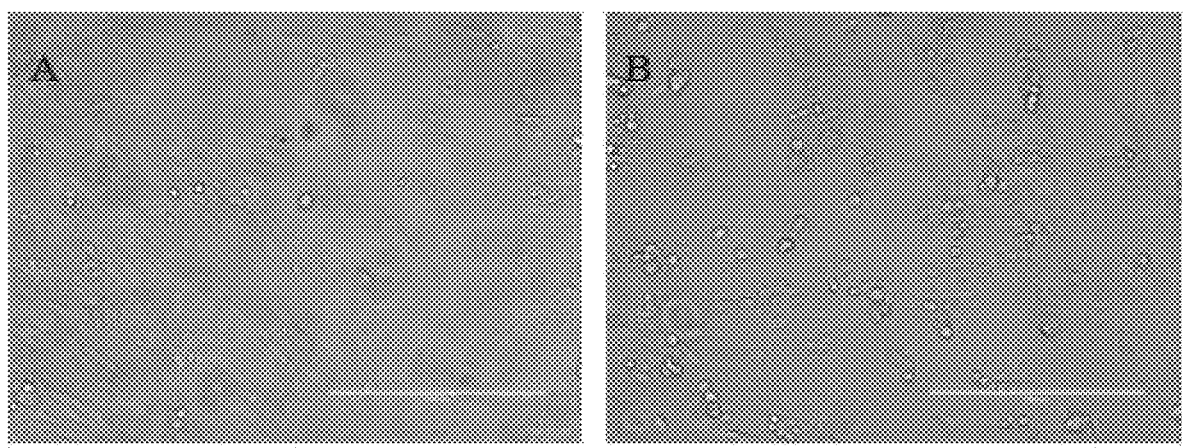
FIG. 3 shows the cytopathic effect (CPE) of BHK-21 cells infected by the recombinant virus rSVV/FJ-M strain in Example 2, wherein "A" represents normal BHK-21 cells; "B" represents BHK-21 cells with CPE.

Rescue of Recombinant Seneca Valley Virus and Culture Characteristics of Different Cells 2.1 Rescue of Recombinant Seneca Valley Virus The recombinant plasmid prSVV/FJ-M obtained in Example 1 was prepared by plasmid extraction kit and used for transfection when BHK-21 cells grow to 80% in confluence. Using the liposome transfection reagents, 4 μg of the recombinant plasmid was transfected into BHK-21 cells. At the same time, a liposome control and a normal cell control were set up and placed in a 37° C. incubator containing 5% $CO_2$. After transfection for 6 h, the supernatant was discarded, and MEM medium was added, the culture was continued and the cell state and cytopathic effect were observed. When the cytopathic effect reached about 90%, the cell culture was harvested, and then frozen and thawed for 3 times. BHK-21 cells were inoculated with the virus and passaged repeatedly until the virus could stably induce cytopathic effect, such as, the cells became round and fall off, and gradually formed plaque and disintegrated into fragments. The obtained recombinant virus was named rSVV/FJ-M (as shown in FIG. 3).

2.2 Culture Characteristics of Recombinant Seneca Valley Virus in Different Cells The recombinant Seneca valley virus rSVV/FJ-M strain rescued in 2.1 step was used to infect different cells, and it was found that the recombinant virus strain could proliferate in BHK-21 cells, PK-15 cells, ST cells, SK-RST cells, IBRS-2 cells, H1299 cells or 293 T cells, and cause typical cytopathic effect, which had similar culture characteristics in different cells to the wild parental virus strain SVV/FJ/001.

Example 3

Identification of Recombinant Seneca Valley Virus by RT-PCR

Total RNA was extracted from the supernatant of BHK-21 cells infected with stably passaged rSVV/FJ-M strain by Trizol reagent or RNA extraction kit. After reverse transcription, P1 gene and S1 gene comprising 5'UTR were amplified, then purified, collected and sent for sequencing. The results showed that the obtained P1 gene was consistent with the reference sequence of SVV/FJ/001 strain, and the 5'UTR gene was consistent with the theoretical sequence.

Example 4

Pathogenicity Test of Recombinant Seneca Valley Virus

4.1 Pathogenicity Test of Recombinant Seneca Valley Virus on Cells

Susceptible cells of SVA, such as BHK-21 cells, PK-15 cells, ST cells, IBRS-2 cells in Example 2, were digested according to the conventional method, and DMEM complete medium comprising 10% fetal bovine serum was added. The cells were split into a 12-well plate and cultured in an incubator comprising 5% $CO_2$ at 37° C. until the monolayer cells grow to 80%-90% in confluence, for later use. The virus solution was diluted with DMEM at a 10-fold serial dilution, and the virus solution with different dilutions ($10^{-5.0}$-$10^{-10.0}$) was added to the cell plate, with 4 wells for each dilution, and then cultured in an incubator containing 5% $CO_2$ at 37° C. for 4 days. Reed-Muench's method was used to determine the median infective dose ($TCID_{50}$) of the virus to different cells such as BHK-21 cell. According to the virus titers of rSVV/FJ-M strain on different cells such as BHK-21 cell determined by the method, the $TCID_{50}$ of rSVV/FJ-M strain was calculated to be $10^{-6.5}$/mL-$10^{-10.0}$/mL.

According to this method, the virus titers in BHK-21 and other different cells were determined, and the Reed-Muench's method can be seen in the literature "Reed, L. J. and Muench, H. (1938). "A Simple Method of Estimating Fifty Percent Endpoints". The American Journal of Hygiene 27: 493-497".

4.2 Pathogenicity Test of Recombinant Seneca Valley Virus to Pigs

Twelve pigs were screened from Seneca valley virus non-epidemic areas and determined by the neutralizing experiment, and the neutralizing antibody titer of Seneca valley virus was less than 1:4. According to the conditions of the established viral challenge model of SVV/FJ/001 strain to pigs, the prepared rSVV/FJ-M strain was used for viral challenge by injection, and the challenge dose was set to three gradients, which were $2 \times 10^9$ $TCID_{50}$, $6 \times 10^9$ $TCID_{50}$, $2 \times 10^{10}$ $TCID_{50}$, and the SVV/FJ/001 cell strain was set as control, with the challenge dose of $2 \times 10^9$ $TCID_{50}$, 2 mL/pig. All the groups were observed continuously for 13 days, and the clinical manifestation was observed and recorded, the clinical manifestation of animals can be judged according to the symptoms such as blisters on hoof, nose and lips, and scored (5-point system, the judgment standard was made according to the scoring standard of foot-and-mouth disease, and the higher the score, the severer the clinical symptoms were). The viral challenge results showed that the control wild parental strain SVV/FJ/001 showed typical clinical symptoms from the second day after viral challenge, with blisters on the hoof and then blisters on the nose. However, after the recombinant Seneca valley virus rSVV/FJ-M strain challenge, there were no clinical symptoms in the three challenge dose groups, and the results were shown in Table 1.

TABLE 1

Clinical symptoms of pathogenicity test of recombinant Seneca valley virus to pigs

| Group | challenge dose | Serial number | 1 d | 2 d | 3 d | 4 d | 5 d | 6 d | 7 d | 8 d | 9 d | 10 d | 11 d | 12 d | 13 d |
|---|---|---|---|---|---|---|---|---|---|---|---|---|---|---|---|
| rSVV/FJ-M strain | $2 \times 10^9$ $TCID_{50}$ | P030 | — | — | — | — | — | — | — | — | — | — | — | — | — |
| | | P033 | — | — | — | — | — | — | — | — | — | — | — | — | — |
| | | P038 | — | — | — | — | — | — | — | — | — | — | — | — | — |
| rSVV/FJ-M strain | $6 \times 10^9$ $TCID_{50}$ | P031 | — | — | — | — | — | — | — | — | — | — | — | — | — |
| | | P034 | — | — | — | — | — | — | — | — | — | — | — | — | — |
| | | P035 | — | — | — | — | — | — | — | — | — | — | — | — | — |
| rSVV/FJ-M strain | $2 \times 10^{10}$ $TCID_{50}$ | P032 | — | — | — | — | — | — | — | — | — | — | — | — | — |
| | | P037 | — | — | — | — | — | — | — | — | — | — | — | — | — |
| | | P039 | — | — | — | — | — | — | — | — | — | — | — | — | — |
| SVV/FJ/001 strain (control) | $2 \times 10^9$ $TCID_{50}$ | P036 | — | — | 2 | 2 | 2 | 4 | 4 | 4 | 4 | 4 | 4 | 4 | 4 |
| | | P040 | — | — | — | 1 | 3 | 3 | 3 | 3 | 3 | 3 | 3 | 3 | 3 |
| | | P041 | — | 2 | 2 | 4 | 4 | 5 | 5 | 5 | 5 | 5 | 5 | 5 | 5 |

Example 5

Suspension Cell Culture of Recombinant Seneca Valley Virus:

5.1 Sensitivity Test of BHK-21 Suspension Cells to Recombinant Seneca Valley Virus The suspended BHK-21-S cells (disclosed in the patent application "Method for preparing Seneca valley virus by using suspended cell lines" (CN application number: 201910935029.1), the disclosure of which is incorporated by reference herein in its entirety as part of the present application) was inoculated with recombinant Seneca valley virus rSVV/FJ-M for culture. After the cell density grow to $3.0$-$3.5 \times 10^6$ cell/ml, the appropriate temperature, pH value, rotational speed and the like were set, the recombinant Seneca valley virus was inoculated to the cells using a 1% volume dose. The cell morphology was observed through regular sampling, when the cell viability was lower than 20%, the virus was harvested to measure the $TCID_{50}$ of the virus (Table 2). The results showed that the recombinant Seneca valley virus strain had good sensitivity of infection and proliferation in suspension BHK-21-S cells, could adapt well in the cells, having the characteristics of short cytopathic effect time and high virus titers. After five consecutive generations of suspension cell passage, the RT-PCR amplification sequencing comparison showed that the nucleotide sequence of the strain was consistent with that of the virus before suspension cell culture, which indicated that the strain had good stability and could be used for the production and preparation of recombinant Seneca valley virus antigen.

TABLE 2

Adaptation results of suspension culture of recombinant Seneca valley virus

| Generations | BHK-SF1 | BHK-SF2 | BHK-SF3 | BHK-SF4 | BHK-SF5 |
|---|---|---|---|---|---|
| $TCID_{50}$/ml | $10^{-7.67}$ | $10^{-8.50}$ | $10^{-8.83}$ | $10^{-8.77}$ | $10^{-9.0}$ |

5.2 Sensitivity Test of ST Suspension Cells to Recombinant Seneca Valley Virus

The suspended ST-S cells (disclosed in the patent application "Method for preparing Seneca valley virus by using suspended cell lines" (CN application number: 201910933902.3), the disclosure of which is incorporated by reference herein in its entirety as part of the present application) was inoculated with recombinant Seneca valley virus rSVV/FJ-M for culture. After the cell density grows to 3.0-3.5×10$^6$ cell/ml, the appropriate temperature, pH value, rotational speed and the like were set, the recombinant Seneca valley virus was inoculated to the cells using a 1% volume dose. The cell morphology was observed through regular sampling, when the cell viability was lower than 20%, the virus was harvested to measure the $TCID_{50}$ of the virus (Table 3). The results showed that the recombinant Seneca valley virus strain had good sensitivity of infection and proliferation in suspension ST-S cells, could adapt well in the cells, having the characteristics of short cytopathic effect time and high virus titers. After five consecutive generations of suspension cell passage, the RT-PCR amplification sequencing comparison showed that the nucleotide sequence of the strain was consistent with that of the virus before suspension cell culture, which indicated that the strain had good stability and could be used for the production and preparation of recombinant Seneca valley virus antigen.

TABLE 3

Adaptation results of suspension culture of recombinant Seneca valley virus

| Generations | ST-SF1 | ST-SF2 | ST-SF3 | ST-SF4 | ST-SF5 |
|---|---|---|---|---|---|
| $TCID_{50}$/ml | $10^{-7.50}$ | $10^{-8.41}$ | $10^{-8.5}$ | $10^{-8.83}$ | $10^{-9.0}$ |

Example 6

Preparation and Immune Efficacy Evaluation of Recombinant Seneca Valley Virus Vaccine 6.1 Vaccine Preparation 6.1.1 Preparation of virus solution: the obtained rSVV/FJ-M strain was cultured according to the method of Example 2 or Example 5. During adherent cell culture, the virus was inoculated into susceptible cells which had formed monolayer according to a 1% volume dose of the culture solution, when the cytopathic effect reaches more than 80%, the virus-containing cell culture solution was harvested, frozen and thawed for 3 times, and stored at −70° C. for later use. In suspension cell culture, Seneca valley virus was inoculated at a 1% volume dose, when the cell viability was lower than 20%, the virus culture solution was harvested, frozen and thawed for 3 times, and stored at −70° C. for later use. The virus content was determined as described in Example 4, and the $TCID_{50}$ of the virus was calculated according to Reed-Muench method. As a result, the virus titer of the recombinant Seneca valley virus was not lower than $10^{6.5}$ $TCID_{50}$/mL.

6.1.2 Inactivation: The inactivation was performed with 1.5 mmol/L binary ethylenimine (BEI) at 30° C. for 36 h, then the blocking agent sodium thiosulfate solution was added, the solution was maintained overnight at 4° C., and stored for later use. At the same time, the inactivated virus solution was blindly transmitted to Seneca valley virus susceptible cells for three generations for inactivation check, and live virus control and normal cell control were set up. As a result, the inactivated virus solution could not cause pathological changes in susceptible cells.

6.1.3 Preparation of vaccine: Inactivated and inactivation-checked antigen was emulsified with the oil adjuvant at a ratio of 1:1 to prepare an oil-in-water vaccine, which was packed separately for later use.

6.1.4 Safety test: The experimental pigs were purchased from Seneca valley virus non-epidemic areas and determined by the neutralizing experiment, the neutralizing antibody titer of Seneca valley virus was less than 1:4. Two nursery pigs were vaccinated with 6 mL of the recombinant inactivated virus vaccine through intramuscular injection, and the uninfected pigs with the same conditions were set as control, all of which were observed continuously for 28 days. During the observation period, the immunized pigs were in good health without any local or systemic adverse reactions after vaccine injection.

6.2 Protection Test of Viral Challenge after Vaccine Immunization 10 pigs were immunized with the inactivated and safety checked vaccine of recombinant Seneca valley virus, and 3 non-immune controls were set to measure its immune efficacy. The experimental pigs were purchased from Seneca valley virus non-epidemic areas and determined by the neutralizing experiment, the neutralizing antibody titer of Seneca valley virus was less than 1:4. After immunization of the animals, blood was collected to separate the serum on the 7th day, 14th day, 21st day and 28th day after immunization. The results showed that the vaccine had good immunogenicity and could effectively induce the production of neutralizing antibody in the serum (Table 4).

TABLE 4

Detection results of neutralizing antibody level after immunization with recombinant Seneca valley virus vaccine

| Serial number | Immunization dose (mL) | Neutralizing antibody titer | | | | |
|---|---|---|---|---|---|---|
| | | 0 d | 7 d | 14 d | 21 d | 28 d |
| PA061 | 2 | <4 | 90 | 256 | 512 | 512 |
| PA062 | 2 | <4 | 45 | 90 | 360 | 360 |
| PA063 | 2 | <4 | 128 | 256 | 512 | 720 |
| PA064 | 2 | <4 | 90 | 256 | 720 | 720 |
| PA065 | 2 | <4 | 180 | 360 | 720 | 1024 |

TABLE 4-continued

Detection results of neutralizing antibody level after immunization with recombinant Seneca valley virus vaccine

| Serial number | Immunization dose (mL) | Neutralizing antibody titer | | | | |
|---|---|---|---|---|---|---|
| | | 0 d | 7 d | 14 d | 21 d | 28 d |
| PA066 | 2 | <4 | 90 | 256 | 360 | 360 |
| PA067 | 2 | <4 | 64 | 128 | 512 | 720 |
| PA068 | 2 | <4 | 128 | 180 | 720 | 1024 |
| PA069 | 2 | <4 | 45 | 45 | 128 | 180 |
| PA070 | 2 | <4 | 180 | 256 | 720 | 1024 |
| PA071 | 0 | <4 | <4 | <4 | <4 | <4 |
| PA072 | 0 | <4 | <4 | <4 | <4 | <4 |
| PA073 | 0 | <4 | <4 | <4 | <4 | <4 |

At 28 days after immunization of pigs, the viral challenge experiment was carried out with a dose of $2\times10^9$ TCID$_{50}$ SVV/FJ/001 strain, which was observed continuously for 13 days. The results showed that the immunized animals had no clinical symptoms and were 100% protected, as shown in Table 5.

TABLE 5

Clinical symptoms and protection of pigs immunized with Seneca recombinant inactivated virus vaccine after viral challenge

| No. | Immunization dose (mL) | 1dpc | 2dpc | 3dpc | 4dpc | 5dpc | 6dpc | 7dpc | 8dpc | 9dpc | 10dp | 11dp | 12dp | 13dp | Protected or not |
|---|---|---|---|---|---|---|---|---|---|---|---|---|---|---|---|
| PA061 | 2 | — | — | — | — | — | — | — | — | — | — | — | — | — | Yes |
| PA062 | 2 | — | — | — | — | — | — | — | — | — | — | — | — | — | Yes |
| PA063 | 2 | — | — | — | — | — | — | — | — | — | — | — | — | — | Yes |
| PA064 | 2 | — | — | — | — | — | — | — | — | — | — | — | — | — | Yes |
| PA065 | 2 | — | — | — | — | — | — | — | — | — | — | — | — | — | Yes |
| PA066 | 2 | — | — | — | — | — | — | — | — | — | — | — | — | — | Yes |
| PA067 | 2 | — | — | — | — | — | — | — | — | — | — | — | — | — | Yes |
| PA068 | 2 | — | — | — | — | — | — | — | — | — | — | — | — | — | Yes |
| PA069 | 2 | — | — | — | — | — | — | — | — | — | — | — | — | — | Yes |
| PA070 | 2 | — | — | — | — | — | — | — | — | — | — | — | — | — | Yes |
| PA071 | 0 | — | — | 2 | 3 | 5 | 5 | 5 | 5 | 5 | 5 | 5 | 5 | 5 | No |
| PA072 | 0 | — | — | — | 1 | 1 | 3 | 4 | 4 | 4 | 4 | 4 | 4 | 4 | No |
| PA073 | 0 | — | — | 1 | 2 | 2 | 2 | 3 | 4 | 4 | 4 | 4 | 4 | 4 | No |

6.3 Vaccine Immune Efficacy and Cross-Challenge Test

The pigs used in this test were purchased from Seneca valley virus non-epidemic areas, and the neutralizing antibody titer of Seneca valley virus was less than 1:4, and the animals were kept in ABSL-3 laboratory strictly. According to the determination method of PD$_{50}$ recorded in Chinese Veterinary Pharmacopoeia in 2015, the specific method was as follows: 15 pigs in each immunization group, the immunization dose was divided into 1 dose, 1/3 dose and 1/9 dose, and 5 pigs were immunized with each immunization dose respectively. At 28 days after immunization, the SVV/FJ/001 strain, Henan strain of Seneca valley virus (SVV-HN strain) and Guangdong strain of Seneca valley virus (SVV-GD strain) were used to challenge animals, and the challenge dose was $2\times10^9$ TCID$_{50}$, 3 pigs was set as control in each group, and the viral challenge way was intramuscular injection. After viral challenge, all the groups were continuously observed for 15 days, the clinical manifestation of the animals was judged by the symptoms such as blisters on nose, lips and hoofs, once clinical manifestation observed, the animals were judged as unprotected. The protection ratio of immunized animals in each group was calculated, and finally the PD$_{50}$ of each group was calculated according to Reed-Muench method.

The results of immune efficacy and cross-challenge test showed that the PD$_{50}$ of the vaccine strain to SVV/FJ/001 strain, SVV-HN strain and SVV-GD strain were 15.59, 13.59 and 13.59, respectively (Table 6), which indicated that the PD$_{50}$ value of the vaccine against epidemic viruses in different provinces was all greater than 6, it was an ideal vaccine against Seneca valley virus and can be used for preventing and controlling Seneca valley virus in China and the neighboring countries.

TABLE 6

Immune efficacy and cross-challenge protection results of recombinant Seneca valley virus vaccine strain

| Groups | Immunization dose | Challenge strain | Protection ratio | PD$_{50}$ |
|---|---|---|---|---|
| Group 1 | 1 | SVV/FJ/001 strain | 5/5 | 15.59 |
| | 1/3 | SVV/FJ/001 strain | 5/5 | |
| | 1/9 | SVV/FJ/001 strain | 5/5 | |
| Control group 1 | 0 | SVV/FJ/001 strain | 0/3 | |
| Group 2 | 1 | SVV-HN strain | 5/5 | 13.59 |
| | 1/3 | SVV-HN strain | 5/5 | |
| | 1/9 | SVV-HN strain | 4/5 | |
| Control group 2 | 0 | SVV-HN strain | 0/3 | |
| Group 3 | 1 | SVV-GD strain | 5/5 | 13.59 |
| | 1/3 | SVV-GD strain | 5/5 | |
| | 1/9 | SVV-GD strain | 4/5 | |
| Control group 3 | 0 | SVV-GD strain | 0/3 | |

The above is only the preferred embodiment of the present disclosure, and it should be pointed out that for ordinary skills in the technical field, without departing from the principle of the present disclosure, several improvements and embellishments can be made, and these improvements and embellishments should also be regarded as the protection scope of the present disclosure.

What is claimed is:

1. A recombinant nucleic acid of Seneca valley virus, wherein the sequence of the recombinant nucleic acid is a viral genome sequence obtained by performing deletion and mutation on 5'UTR gene sequence of the Seneca valley virus strain;
the nucleotide sequence of the 5'UTR gene after deletion and mutation on the 5'UTR gene sequence of the Seneca valley virus strain is set forth in SEQ ID NO:1; and
the Seneca valley virus strain is SW/FJ/001 strain.

2. A recombinant Seneca valley virus comprising the recombinant nucleic acid according to claim 1.

3. A recombinant Seneca valley virus encoded by the recombinant nucleic acid according to claim 1.

4. A recombinant Seneca valley virus vaccine strain comprising the recombinant Seneca valley virus according to claim 3.

5. A method of constructing the recombinant Seneca valley virus according to claim 3, comprising:
(1) using a cDNA of SW/FJ/001 strain as template, a S1 fragment and a S2 fragment of SW/FJ/001 strain are generated using specific primer pairs respectively; the specific primer pair for amplifying the S1 fragment comprise two forward primers and a reverse primer SVA-1R, wherein the forward primers comprises SVA-1F0 and SVA-1F; the nucleotide sequence of the forward primer SVA-1F0 is set forth in SEQ ID NO:2, the nucleotide sequence of the forward primer SVA-1F is set forth in SEQ ID NO:3, and the nucleotide sequence of the reverse primer SVA-1R is set forth in SEQ ID NO:4;
a specific primer pair for amplifying the S2 fragment comprises a forward primer SVA-2F and a reverse primer SVA-2R, wherein the nucleotide sequence of the forward primer SVA-2F is set forth in SEQ ID NO:5, and the nucleotide sequence of the reverse primer SVA-2R is set forth in SEQ ID NO:6;

(2) ligating the S1 fragment and S2 fragment with pMD20 T vector respectively to obtain subclone plasmids PMD-S1 and PMD-S2;

(3) using the subclone plasmid PMD-S1 as a template, amplifying the PMD-S1 with mutation primers SVA-m5UTRF and SVA-m5UTRR to obtain subclone plasmid PMD-mS1, wherein the nucleotide sequence of SVA-m5UTRF is set forth in SEQ ID NO:7, and the nucleotide sequence of SVA-m5UTRR is set forth in SEQ ID NO:8;

(4) after digesting the plasmid PMD-mS1 with PacI and SphI, and digesting the plasmid PMD-S2 with SphI and NotI, collecting the gene fragments and inserting into eukaryotic transcription plasmid prO/CHA/99 digested with PacI and NotI, thus obtaining the recombinant plasmid prSVV/FJ-M; and (5) transfecting the Seneca valley virus sensitive cells with the obtained eukaryotic transcription plasmid prSVV/FJ-M to obtain the recombinant Seneca valley virus.

6. A preparation method of recombinant Seneca valley virus vaccine, comprising:
1) Inoculating recombinant Seneca valley virus according to claim 3 into susceptible cells for proliferation of the virus to obtain a recombinant Seneca valley virus solution; the susceptible cells comprise suspension cells of BHK-21 cells, PK-15 cells, ST cells, SK-RST cells, IBRS-2 cells, H1299 cells or 293T cells; and
2) inactivating and emulsifying the recombinant Seneca valley virus in the recombinant Seneca valley virus solution to obtain the recombinant Seneca valley virus vaccine.

7. The recombinant Seneca valley virus vaccine prepared by the preparation method according to claim 6.

8. The recombinant Seneca valley virus vaccine strain according to claim 4, wherein the values of the 50% protection dose ($PD_{50}$) of the recombinant Seneca valley virus vaccine strains against the Seneca valley virus isolates are all greater than 6.

9. The constructing method according to claim 5, wherein the Seneca valley virus sensitive cells in step (5) comprises BHK-21 cells, PK-15 cells, ST cells, SK-RST cells, IBRS-2 cells, H1299 cells or 293T cells.

10. The constructing method according to claim 5, wherein the recombinant Seneca valley virus obtained in step (5) is suitable for suspension cell culture.

11. The preparation method according to claim 6, wherein during the proliferation culture in step 1), the virus titer of the recombinant Seneca valley virus is not lower than $10^{6.5}$ $TCID_{50}$/mL.

12. The preparation method according to claim 6, wherein the inactivation in step 2) is carried out by using binary ethylenimine.

13. The preparation method according to claim 12, wherein the concentration of the binary ethylenimine in the inactivated system is 1.5 mmol/L.

14. The preparation method according to claim 13, wherein a temperature of the inactivating step is 30° C., and a duration of the inactivating step is 36 hours.

15. The preparation method according to claim 6, wherein during the emulsification in step 2), the inactivated recombinant Seneca valley virus and ISA 206 adjuvant are mixed in a volume ratio of 1:1.

\* \* \* \* \*

UNITED STATES PATENT AND TRADEMARK OFFICE
CERTIFICATE OF CORRECTION

PATENT NO. : 11,883,482 B2  
APPLICATION NO. : 17/328135  
DATED : January 30, 2024  
INVENTOR(S) : Zheng et al.

Page 1 of 1

It is certified that error appears in the above-identified patent and that said Letters Patent is hereby corrected as shown below:

In the Claims

Column 19, Claim 4, Line 57, delete "claim 3" and insert -- claim 2 --.

Column 19, Claim 5, Line 59, delete "claim 3" and insert -- claim 2 --.

Column 21, Claim 6, Line 8, delete "claim 3" and insert -- claim 2 --.

Signed and Sealed this  
Twenty-seventh Day of August, 2024

Katherine Kelly Vidal  
*Director of the United States Patent and Trademark Office*

SEQUENCE LISTING

<160> NUMBER OF SEQ ID NOS: 8

<210> SEQ ID NO 1
<211> LENGTH: 655
<212> TYPE: DNA
<213> ORGANISM: Artificial Sequence
<220> FEATURE:
<223> OTHER INFORMATION: mutated 5'UTR gene fragment

<400> SEQUENCE: 1

```
ttgaaagggg gggctgggcc ctcatgccca gtccttcctt tccccttccg gggggtaaac    60
cggctgtgtt tgctagaggc acagaggagc aacatccaac ctgcttttgt ggggaacagt   120
gcggctccaa ttcctgcgtc gccaaaggtg ttagcgcacc caaacggcgc atctaccaat   180
gctattggtg tggtctgcga gttctagcct actcgttttt tccccactc actcattcgt    240 gttgtaacta caggatttgg ccctcgcacg ggatgtgcga taaccgcaag attgactcaa   300
gcgcggaaag cgttgtaacc acatgctgtt agtcccttta tggctgtgag atggctatcc   360
acctcggatc actgaactgg agctcgaccc tccttagtaa gggaaccgag aggccttcct   420
gcaacaagct ccgacacaga gtccacgtga ttgctaccac catgagtaca tggttctccc   480
ctctcgaccc aggacttctt tttgaatatc cacggctcga tccagagggt ggggcatgat   540 cccccctagca tagcgagcta cagcgggaac tgtagctagg ccttagcgtg ccttggatac   600
tgcctgatag ggcgacggcc tagtcgtgtc ggttctatag gtagcacata caaat         655
```

<210> SEQ ID NO 2
<211> LENGTH: 57
<212> TYPE: DNA
<213> ORGANISM: Artificial Sequence
<220> FEATURE:
<223> OTHER INFORMATION: Forward primer of the specific primer pair that
amplifies S1 fragment: SVA-1F0

<400> SEQUENCE: 2

```
gtgaggacga aactatagga aaggaattcc tatagtcttg aaaggggggg ctgggcc       57
```

<210> SEQ ID NO 3
<211> LENGTH: 55
<212> TYPE: DNA
<213> ORGANISM: Artificial Sequence
<220> FEATURE:
<223> OTHER INFORMATION: Forward primer of the specific primer pair that
amplifies S1 fragment: SVA-1F

<400> SEQUENCE: 3

```
ataggtttaa ttaatgttaa gcgtctgatg agtccgtgag gacgaaacta tagga         55
```

<210> SEQ ID NO 4
<211> LENGTH: 26
<212> TYPE: DNA
<213> ORGANISM: Artificial Sequence
<220> FEATURE:
<223> OTHER INFORMATION: Reverse primer of the specific primer pair that
amplifies S1 fragment: SVA-1R

<400> SEQUENCE: 4

```
gggaagcatg ctggggcacc aggcac                                         26
```

<210> SEQ ID NO 5
<211> LENGTH: 25
<212> TYPE: DNA
<213> ORGANISM: Artificial Sequence
<220> FEATURE:

```
<223> OTHER INFORMATION: Forward primer of the specific primer pair that
      amplifies S2 fragment: SVA-2F

<400> SEQUENCE: 5
ccccagcatg cttccctttc gcagc                                           25

<210> SEQ ID NO 6
<211> LENGTH: 55
<212> TYPE: DNA
<213> ORGANISM: Artificial Sequence
<220> FEATURE:
<223> OTHER INFORMATION: Reverse primer of the specific primer pair that
      amplifies S2 fragment: SVA-2R

<400> SEQUENCE: 6
ttttctagag cggccgcttt tttttttttt tttttttttt tttttttttt ttttt         55

<210> SEQ ID NO 7
<211> LENGTH: 56
<212> TYPE: DNA
<213> ORGANISM: Artificial Sequence
<220> FEATURE:
<223> OTHER INFORMATION: Mutation primer SVA-m5UTRF

<400> SEQUENCE: 7
gttctagcct actcgttttt tcccctactc actcattcgt gttgtaacta caggat       56

<210> SEQ ID NO 8
<211> LENGTH: 56
<212> TYPE: DNA
<213> ORGANISM: Artificial Sequence
<220> FEATURE:
<223> OTHER INFORMATION: Mutation primer SVA-m5UTRR

<400> SEQUENCE: 8
atcctgtagt tacaacacga atgagtgagt agggaaaaa acgagtaggc tagaac         56
```